United States Patent [19]

Mantegani et al.

[11] 4,321,381
[45] * Mar. 23, 1982

[54] ERGOT DERIVATIVES

[75] Inventors: Sergio Mantegani; Guiliana Arcari; Anna M. Caravaggi; Germano Bosisio, all of Milan, Italy

[73] Assignee: Farmitalia Carlo Erba S.p.A., Italy

[*] Notice: The portion of the term of this patent subsequent to Feb. 24, 1998, has been disclaimed.

[21] Appl. No.: 188,620

[22] Filed: Sep. 19, 1980

Related U.S. Application Data

[63] Continuation-in-part of Ser. No. 72,289, Sep. 4, 1979, Pat. No. 4,252,941.

[30] Foreign Application Priority Data

Sep. 8, 1978 [GB] United Kingdom ............... 36080/78

[51] Int. Cl.³ .................. A61K 31/48; A61K 31/495; C07D 457/02
[52] U.S. Cl. ..................................... 546/67; 544/125; 544/361; 546/68; 424/248.57; 424/250; 424/261
[58] Field of Search .................. 544/125, 361; 546/67, 546/68

[56] References Cited

U.S. PATENT DOCUMENTS 3,985,752 10/1976 Kornfeld et al. ............... 546/67
4,064,130 12/1977 Semonsky et al. ............. 546/67
4,166,911 9/1979 Bernardi et al. ............... 546/67
4,252,941 2/1981 Mantegani et al. ............ 544/361

OTHER PUBLICATIONS

Smith, Open-Chain Nitrogen Compounds, vol. 1, (W. A. Benjamin, Inc., N.Y., 1965), p. 63.

Primary Examiner—Alton D. Rollins
Attorney, Agent, or Firm—Stevens, Davis, Miller & Mosher

[57] ABSTRACT

Compounds and process for making same are disclosed, the compounds having the formula (I):

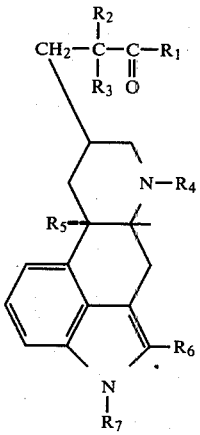

wherein $R_1$ represents methyl, phenyl, piperidino, 1-pyrrolidinyl, morpholino or 4-methyl-1-piperazinyl, alkyl or alkoxy having from 1 to 4 carbon atoms, amino, substituted amino of the formula NHR' (wherein R' is alkyl having from 1 to 4 carbon atoms, cycloalkyl, a benzyl, or phenyl) or substituted amino of the formula NR" R''' (wherein R" and R''' both represent alkyl having from 1 to 4 carbon atoms);

$R_2$ represents a hydrogen atom, alkyl having from 1 to 4 carbon atoms, or phenyl;

$R_3$ represents a fluorine atom, cyano, difluoromethyl, difluorobromomethyl, trifluoromethyl, methylthio, methylsulphonyl, sulphonamido, an alkoxy having from 1 to 4 carbon atoms, an alkanoyl having from 2 to 5 carbon atoms, or benzoyl;

$R_4$ represents a hydrocarbon having from 1 to 4 carbon atoms;

$R_5$ represents a hydrogen atom or methoxy;

$R_6$ represents a hydrogen or halogen atom or methyl; and $R_7$ represents a hydrogen atom or methyl. The 2-cyano derivatives are especially preferred.

The compounds are useful as antihypertensive agents.

21 Claims, No Drawings

ERGOT DERIVATIVES

CROSS REFERENCE TO RELATED APPLICATION

This application is a continuation-in-part of copending application Ser. No. 72,289, filed Sept. 4, 1979, now U.S. Pat. No. 4,252,941, issued Feb. 24, 1981.

DESCRIPTION OF THE INVENTION

This invention relates to ergoline derivatives and processes for their preparation.

The invention provide ergoline derivatives of the formula (I):

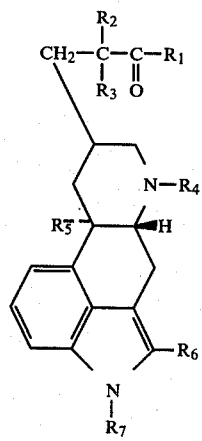

wherein $R_1$ represents a methyl, phenyl, piperidino, 1-pyrrolidinyl, morpholino or 4-methyl-1-piperazinyl, alkyl or alkoxy having from 1 to 4 carbon atoms, amino, substituted amino of the formula NHR' (wherein R' represents alkyl having from 1 to 4 carbon atoms, cycloalkyl, benzyl, or phenyl) or substituted amino of the formula NR" R'" (wherein R and R'" both represent alkyl having from 1 to 4 carbon atoms);

$R_2$ represents a hydrogen atom, alkyl having from 1 to 4 carbon atoms, or phenyl;

$R_3$ represents a fluorine atom, cyano, difluoromethyl, difluorobromomethyl, trifluoromethyl, methylthhio, methylsulfonyl, sulphonamido, alkoxy having from 1 to 4 carbon atoms, alkanoyl having from 2 to 5 carbon atoms, or benzoyl;

$R_4$ represents a hydrocarbon having from 1 to 4 carbon atoms;

$R_5$ represents a hydrogen atom or methoxy;

$R_6$ represents a hydrogen or halogen atom or methyl; and $R_7$ represents a hydrogen atom or methyl.

In the definition of $R_4$, a hydrocarbon group having from 1 to 4 carbon atoms is intended to include alkyl, cycloalkyl, and unsaturated (both ethylenically and acetylenically) groups. Representative moieties include methyl, ethyl, n-propyl, isopropyl, butyl, t-butyl, isobutyl, cyclopropyl, methylcyclopropyl, vinyl, allyl, and propargyl.

Ergoline derivatives of the formula (I) as above defined may be prepared by condensing a compound of the formula (II) below with an alkaline salt of a compound of the formula (III) below. In the formulae (II) and (III), $R_1$, $R_2$, $R_3$, $R_4$, $R_5$, $R_6$, and $R_7$ have the meanings given above.

The compounds of formula (II) are well-known in the art or can be made from precursor compounds by well-known reactions. See, for example, J. Krepelka et al., Vol. 42, Collection Czechoslav. Chem. Comm., pages 1209 to 1212 (1977) and L. Bernardi et al., "Il Farmaco," No. 10, pages 789 to 795 (October 1975).

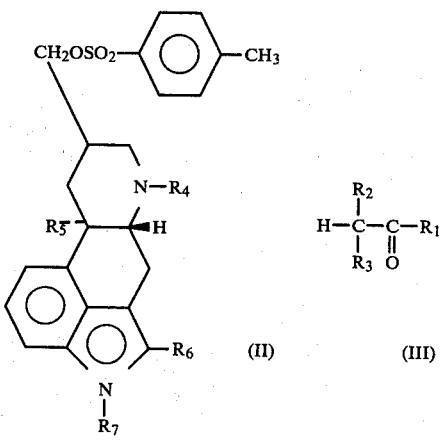

The condensation process, which is also within the scope of the invention, is carried out in a polar aprotic solvent at a temperature of from 50° to 100° C. for 2 to 10 hours. Suitable polar aprotic solvents include dimethylsulphoxide and dimethylformamide.

The condensation is preferably carried out in the presence of sodium or potassium iodide. The condensation products may be purified by conventional procedures. Chromatography over silica gel is especially suitable.

Compounds according to this invention are useful as antihypertensive agents and also have moderate to good antiprolactinic activity.

EVALUATION OF ANTI-HYPERTENSIVE ACTIVITY

1. Spontaneously Hypertensive Rat (MHS)

Four spontaneously hypertensive male rats, strain MHS, weight 250 to 300 g for each group were used. The animals were treated for four consecutive days. The drugs were administered by gastric gavage while suspended in 5% arabic gum (0.2 ml/100 g body weight), and blood pressure (BP) and heart rate (HR) were measured at the tail by BP Recorder W+W. Blood pressure and heart rate were measured on the first and fourth day of treatment 1 hour before and 1 and 5 hours after drug administration. Results are reported in Tables 1 and 2.

2. Normotensive Rat (NR)

Blood pressure recordings have been made in conscious normotensive unrestrained rats weighing approximately 300 g, via a catheter chronically inserted into the left common carotid artery. Implantation of arterial cannula was made under sodium pentobarbital anesthesia (50 mg/kp i.p.) A 1 cm long incision was made through the previously shaved ventral surface of the neck and the tissues overlying the trachea parted by blunt dissection to reveal the carotid artery. The polyethylene catheter used was made with PE 50 tubing, previously filled with saline containing 250 I.U./ml heparin. The tip of the cannula was pushed at least 2 cm inside the vessel toward the heart. The cannula was then firmly tied and passed beneath the skin to emerge from a small incision in the back of the neck. During the post-operative period and before the start of each recording session, the cannula was flushed through daily with saline containing heparin (250 I.U./ml). The experiments were performed two days after surgery. Drugs were administered by gastric gavage. Results are reported in Tables 3 and 4.

Evaluation of the Toxicity (LD$_{50}$)

Ten male mice for each group were orally treated with drugs at different dose levels for the determination of lethal dose 50 (LD$_{50}$). Mice were observed for seven days after administration. LD$_{50}$'s are summarized in Table 5.

TABLE 1

Variation in Blood Pressure in MHS Rats

| Compound | Dose mg/kg os | First Day Change in BP | | Fourth Day Change in BP | |
|---|---|---|---|---|---|
| | | 1 hr after dose (mm Hg) | 5 hrs after dose (mm Hg) | 1 hr after dose (mm Hg) | 5 hrs after dose (mm Hg) |
| 355/1057 (Ex. 8) | 2 | −25 | 0 | −26 | −31 |
| | 5 | −51 | −41 | −45 | −31 |
| 1131 (Ex. 6) | 2 | −26 | −9 | −22 | −25 |
| | 5 | −48 | −43 | −17 | −16 |
| 1133 (Ex. 11) | 2 | −20 | −11 | −21 | −10 |
| | 5 | −24 | −9 | −42 | −25 |
| 1138 (Ex. 5) | 2 | −23 | −14 | −30 | −15 |
| | 5 | −25 | −9 | −26 | −11 |
| 1139 (Ex. 15) | 2 | −13 | −23 | −18 | −12 |
| | 5 | −25 | −24 | −12 | −13 |
| Hydralazine | 2 | +2 | +18 | +7 | +15 |
| | −5 | −52 | −38 | −7 | −8 |
| α-methyl-DOPA | 30 | −3 | −12 | −12 | −19 |
| | +100 | +5 | −38 | −41 | −53 |
| 355/1266 (Ex. 10) | 2 | −14 | −15 | −25 | −45 |
| | 5 | −14 | −10 | −35 | −60 |
| 355/1281 (Ex. 35) | 5 | −25 | −15 | −30 | −35 |
| 355/1282 (Ex. 34) | 2 | −20 | −10 | −15 | −25 |
| | 5 | −40 | −45 | −25 | −30 |
| 355/1320 (Ex. 30) | 5 | −30 | −20 | −20 | −15 |
| 355/1323 (Ex. 45) | 5 | −15 | −20 | −20 | −30 |
| 355/1324 (Ex. 46) | 5 | −20 | −40 | −40 | −35 |
| Example 37 | 5 | −30 | −25 | −45 | −35 |
| Example 38 | 5 | −20 | −10 | −32 | −28 |

TABLE 2

Variation in Heart Rate in MHS Rate

| Compound | Dose mg/kg os | First Day Change in HR (b/min) | | Fourth Day Change in HR (b/min) | |
|---|---|---|---|---|---|
| | | 1 hr after dose | 5 hr after dose | 1 hr after dose | 5 hr after dose |
| 355/1057 | 2 | 0 | −8 | −2 | −5 |
| | 5 | +5 | +35 | +25 | +20 |
| 1131 | 2 | −20 | +5 | −55 | +5 |
| | 5 | −18 | +10 | +18 | −8 |
| 1133 | 2 | −33 | −28 | −20 | −3 |
| | 5 | 0 | +13 | −13 | −8 |
| 1138 | 2 | −25 | −10 | −47 | −12 |
| | 5 | −8 | +5 | −20 | −25 |
| 1139 | 2 | +7 | +12 | +47 | +35 |
| | 5 | +28 | +13 | −10 | −12 |
| Hydralazine | 2 | +10 | −28 | +43 | +23 |
| | 5 | −45 | +12 | +10 | +12 |
| α-methyl-DOPA | 30 | +40 | +15 | +57 | −18 |

TABLE 2-continued

Variation in Heart Rate in MHS Rate

| Compound | Dose mg/kg os | First Day Change in HR (b/min) | | Fourth Day Change in HR (b/min) | |
|---|---|---|---|---|---|
| | | 1 hr after dose | 5 hr after dose | 1 hr after dose | 5 hr after dose |
| | 100 | +87 | +65 | +77 | +37 |

TABLE 3

Variation in Blood Pressure in NR Rats

| Compound | Dose mg/kg os | Change (mm Hg) in Blood Pressure after Treatment | | | | | | |
|---|---|---|---|---|---|---|---|---|
| | | 30′ | 60′ | 120′ | 180′ | 240′ | 360′ | 24h |
| 355/1057 | 5 | −23 | −23 | −22 | −21.7 | −23 | −20 | −12 |
| 1131 | 5 | −22 | −22 | −23 | −20 | −19 | −10 | 0 |
| 1133 | 5 | −15 | −20 | −15 | −10 | −9 | 0 | +5 |
| 1138 | 5 | −10 | −20 | −15 | −10 | −10 | 0 | 0 |
| 1139 | 5 | −5 | −12 | −12 | −10 | −5 | 0 | +2 |
| Hydralazine | 5 | −19 | −13 | −10 | −7 | −5 | −7 | 0 |

TABLE 4

Variation in Heart Rate in NR Rats

| Compound | Dose mg/kg os | Change (b/min) in heart rate after treatment | | | | | | |
|---|---|---|---|---|---|---|---|---|
| | | 30′ | 60′ | 120′ | 180′ | 240′ | 360′ | 24h |
| 355/1057 | 5 | −25 | −40 | −42 | −22 | +10 | +3 | +6 |
| 1131 | 5 | −20 | −30 | −20 | −20 | −10 | +10 | +10 |
| 1133 | 5 | −25 | −45 | −40 | −40 | −10 | −5 | 0 |
| 1138 | 5 | −15 | −30 | −30 | −15 | 0 | +5 | +10 |
| 1139 | 5 | 0 | +10 | +10 | −5 | 0 | +15 | 0 |
| Hydralazine | 5 | +70 | +40 | +21 | +9 | +21 | +12 | +3 |

TABLE 5

| Acute Toxicity LD$_{50}$'s in Mice (mg/kg per os) | |
|---|---|
| 355/1057 | >1000 |
| 1131 | >1000 |
| 1133 | 500 |
| 1138 | 500 |
| 1139 | 125 |
| Hydralazine | 122 |
| α-methyl-DOPA | 5300 |

From the data reported in Table 1 it is apparent that compounds according to the invention induce a consistent blood pressure fall in spontaneously hypertensive rats both at 2 and 5 mg/kg os. This reduction of the blood pressure appears not only on the first day of treatment but also on the fourth day showing absence of tachyphylaxis. Moreover, the reduction lasts at least 5 hours. When compared with hydralazine and α-methyl-DOPA (two known antihypertensive drugs), the new compounds, at the 2 mg/kg level, are more active than hydralazine and more than 15 fold as active as α-methyl-DOPA. At the 5 mg/kg level the new compounds are more active than hydralazine, particularly on the fourth day, and more than 20 fold as active as α-methyl-DOPA. When the variation of the heart rate (HR) is considered, it can be seen (Table 2) that the new compounds induce minor variations whereas α-methyl-DOPA greatly increases it, particularly at the 5 mg/kg level.

The results obtained in the incannulated normotensive rat (Table 3) confirm the antihypertensive activity of the new compounds which compares favorably with that of hyralazine. Moreover, the variations of the heart rate (Table 4) are limited and in any case a favorable reduction rather than an unfavorable increase in the heart rate is observed. Finally, the toxicity of the new compounds, expressed as $LD_{50}$ (Table 5), is no greater than that of hydralazine, being in many cases substantially less, and when the therapeutic ratio (activity versus toxicity) is considered, the new compounds appear to be largely better anti-hypertensive agents than α-methyl-DOPA.

EXAMPLE 1

2-Cyano-3-(6'-methylergoline-8'β)propionic acid ethyl ester (I: $R_1=OCH_2CH_3$, $R_3=CN$, $R_4=CH_3.R_2=R_5=R_6=R_7=H$).

A mixture of 16.9 g of sodium ethyl cyanoacetate, 41 g of 6-methyl-8β-tosyloxymethylergoline and 16 g of potassium iodide in 250 ml of dimethylsulphoxide and 50 ml of ethyl cyanoacetate was heated under stirring at 70° C. for 5 hours. The solution was poured into 7 liters of iced water, and the resultant precipitate was filtered off, dried, and chromatographed on a silica gel column, using chloroform as eluent, to give 24 g of the title compound, m.p. 200°–202° C.

EXAMPLE 2

2-Cyano-3-(6'-methylergoline-8'β)-N-propionylmorpholine (I: $R_1=$ morpholino, $R_3=CN$, $R_4=CH_3$, $R_2=R_5=R_6=R_7=H$)

A mixture of 0.85 g of sodium cyanoacetylmorpholine, 2 g of 6-methyl-8β-tosyloxymethylergoline, 0.6 g of sodium iodide in 10 ml of dimethylsulphoxide and 2 g of cyanoacetylmorpholine was heated under stirring at 80° C. for 10 hours. The solution was poured into 500 ml of water and the resultant precipitate was filtered off, dried, and chromatographed over silica gel to give 1.7 g of the title compound, m.p. 220°–221° C.

EXAMPLE 3

2-Cyano-3-(6'-methylergoline-8'β)-N-phenylpropionamide (I: $R_1=$ anilino, $R_3=CN$, $R_4=CH_3$, $R_2=R_5=R_6=R_7=H$)

Operating as in Example 2, but employing sodium cyanoacetanilide, 2-cyano-3-(6'-methylergoline-8'β)-N-phenylpropionamide, m.p. 180°–181° C., was obtained in 60% yield.

EXAMPLE 4

2-Cyano-3-(6'-methylergoline-8'β)-N-propionyl(N'-methyl)piperazine (I: $R_1=$ 4-methyl-1-piperazinyl, $R_3=CN$, $R_4=CH_3$, $R_2=R_5=R_6=R_7=H$)

Operating as in Example 2, but employing sodium cyanoacetyl-N-methyl-piperazine, the title compound, m.p. 206°–207° C. was obtained in 60% yield.

EXAMPLE 5

2-Cyano-3-(6'-methylergoline-8'β)-N-ethylpropionamide (355/1138) (I: $R_1$—$CH_3CH_2NH$, $R_3=CN$, $R_4=CH_3$, $R_2=R_5=R_6=R_7=H$)

Operating as in Example 2, but employing sodium N-ethyl-cyanoacetamide, the title compound, m.p. 225°–226° C., was obtained in 65% yield.

EXAMPLE 6

2-Cyano-3-(6'-methylergoline-8'β)-N-benzylpropionamide (355/1131) (I: $R_1=C_6H_5CH_2NH$, $R_3=CN$, $R_4=CH_3$, $R_2=R_5=R_6=R_7=H$)

Operating as in Example 2, but employing sodium N-benzyl-cyanacetamide, the title compound, m.p. 233°–234° C., was obtained in 75% yield.

EXAMPLE 7

2-Cyano-3-(6'-methylergoline-8'β)-N-propionyl-piperidine (I: $R_1=$ piperidino, $R_3=CN$, $R_4=CH_3$, $R_2=R_5=R_6=R_7=H$)

Operating as in Example 2, but employing sodium cyanoacetylpiperidine, the title compound, m.p. 252°–253° C., was obtained in 77% yield.

EXAMPLE 8

2-Cyano-3-(6'-methylergoline-8'β)-propionamide (355/1057) (I: $R_1=NH_2$, $R_3=CN$, $R_4=CH_3$, $R_2=R_5=R_6=R_7=H$)

Operating as in Example 2, but employing sodium cyanoacetamide, the title compound, m.p. 248°–250° C., was obtained in 45% yield.

EXAMPLE 9

2-Cyano-3-(6'-ethylergoline-8'β)-propionamide (I: $R_1=NH_2$, $R_3=CN$, $R_4=C_2H_5$, $R_2=R_5=R_6=R_7=H$)

Operating as in Example 8, but employing 6-ethyl-8β-tosyl-oxymethylergoline, the title compound was obtained in 42% yield, m.p. 243°–245° C.

EXAMPLE 10

2-Cyano-3-(6'-allylergoline-8'β)-propionamide (I: $R_1=NH_2$, $R_3=CN$, $R_4=$ allyl, $R_2=R_5=R_6=R_7=H$)

Operating as in Example 8, but employing 6-allyl-8β-tosyl-oxymethylergoline, the title compound was obtained in 40% yield.

EXAMPLE 11

2-Cyano-3-(6'-methylergoline-8'β)-N-propionyl-pyrrolidine (355/1133) (I: $R_1=$ 1-pyrrolidinyl, $R_3=CN$, $R_4=CH_3$, $R_2=R_5=R_6=R_7=H$)

Operating as in Example 2, but employing sodium cyanoacetylpyrrolidine, the title compound, m.p. 219°–220° C., was obtained in 68% yield.

EXAMPLE 12

2-Cyano-3-(1',6'-dimethylergoline-8'β)-propionamide (I: $R_1=NH_2$, $R_3=CN$, $R_4=R_7=CH_3$,
$R_2=R_5=R_6=H$)

Operating as in Example 8, but employing 1,6-dimethyl-8β-tosyloxymethylergoline, the title compound, m.p. 196°–197° C., is obtained in 80% yield.

EXAMPLE 13

2-Cyano-3-(6'-methyl-10'-methoxyergoline-8'β)-propionamide (I: $R_1=NH_2$, $R_3=CN$, $R_4=CH_3$, $R_5=CH_3O$,
$R_2=R_6=R_7=H$)

Operating as in Example 8, but employing 6-methyl-10-methoxy-8β-tosyloxymethylergoline, the title compound m.p. 207°–208° C., was obtained in 45% yield.

EXAMPLE 14

2-Cyano-3-(1',6'-dimethyl-10'-methoxyergoline-8'β)-propionamide (I: $R_1=NH_2$, $R_3=CN$, $R_4=R_7=CH_3.R_2=R_6=H$,
$R_5=CH_3O$).

Operating as in Example 8, but employing 1,6-dimethyl-10-methoxy-8β-tosyloxymethylergoline, the title compound, m.p. 238°–240° C., was obtained in 81% yield.

EXAMPLE 15

2-Cyano-3-(2-bromo-6'-methylergoline-8'β)-propionamide (355/1139) (I: $R_1=NH_2$, $R_3=CN$, $R_4=CH_3$, $R_6=Br$,
$R_2=R_5=R_7=H$)

Operating as in Example 8, but employing 2-bromo-6-methyl-8β-tosyloxymethylergoline, the title compound, m.p. 171°–173° C., was obtained in 41% yield.

EXAMPLE 16

2-Acetyl-3-(6'-methylergoline-8'β)-propionic acid ethyl ester (I: $R_1=OCH_2CH_3$, $R_3=CH_3CO$, $R_4=CH_3$,
$R_2=R_5=R_6=R_7=H$)

Operating as in Example 1, but employing sodium ethyl acetoacetate, the title compound, m.p. 178°–179° C., was obtained in 70% yield.

EXAMPLE 17

3-Acetyl-4-(6'-methylergoline-8'β)-butanone (I: $R_1=R_4=CH_3$, $R_3=CH_3CO$, $R_4=CH_3$,
$R_2=R_5=R_6=R_7=H$)

Operating as in Example 1, but employing sodium acetylacetone, the title compound, m.p. 210°–212° C., was obtained in 75% yield.

EXAMPLE 18

2-Cyano-2-ethyl-3-(6'-methylergoline-8'β)-propionamide (I: $R_1=NH_2$, $R_2=C_2H_5$, $R_3=CN$, $R_4=CH_3$,
$R_5=R_6=R_7=H$)

Operating as in Example 8, but employing sodium ethylcyanoacetamide, the title compound, m.p. 217° C., was obtained in 43% yield.

EXAMPLE 19

2-Cyano-2-phenyl-3-(6'-methylergoline-8'β)-propionamide (I: $R_1=NH_2$, $R_2=C_6H_5$, $R_3=CN$, $R_4=CH_3$,
$R_5=R_6=R_7=H$)

Operating as in Example 8, but employing sodium phenylcyanoacetamide, the title compound, m.p. 232° C., was obtained in 45% yield.

EXAMPLE 20

2-Cyano-3-(1',6'-dimethylergoline-8'β)-N-ethylpropionamide (I: $R_1=CH_3CH_2NH$, $R_3=CN$, $R_4=R_7=CH_3$,
$R_2=R_5=R_6=H$)

Operating as in Example 5, but employing 1,6-dimethyl-8β-tosyloxymethylergoline, the title compound, m.p. 194°–196° C., is obtained in 60% yield.

EXAMPLE 21

2-Cyano-3-(1',6'-dimethylergoline-8'β)-N-propionylpyrrolidine (I: $R_1=$1-pyrrolidinyl, $R_3=CN$, $R_4=R_7=CH_3$,
$R_2=R_5=R_6=H$)

Operating as in Example 11, but employing 1,6-dimethyl-8β-tosyloxymethylergoline, the title compound, m.p. 207°–209° C., is obtained in 55% yield.

EXAMPLE 22

2-Cyano-3-(1',6'-dimethylergoline-8'β)-N-benzylpropionamide (I: $R_1=C_6H_5CH_2NH$, $R_3=CN$, $R_4=R_7=CH_3$,
$R_2=R_5=R_6=H$)

Operating as in Example 6, but employing 1,6-dimethyl-8β-tosyloxymethylergoline, the title compound, m.p. 175°–177° C., is obtained in 40% yield.

EXAMPLE 23

2-Methylsulfonyl-3-(6'-methylergoline-8'β)-propionic acid ethyl ester (I: $R_1=OCH_2CH_3$, $R_3=CH_3SO_2$, $R_4=CH_3$,
$R_2=R_5=R_6=R_7=H$)

Operating as in Example 1, but employing sodium ethylmethylsulfonyl acetate, the title compound, m.p. 199°–201° C., is obtained in 70% yield.

EXAMPLE 24

2-Methylsulfonyl-3-(6'methylergoline-8'β)-N-benzylpropionamide (I: $R_1=C_6H_5CH_2NH$, $R_3=CH_3SO_2$, $R_4=CH_3$,
$R_2=R_5=R_6=R_7=H$)

Operating as in Example 2, but employing sodium N-benzyl-methylsulfonylacetamide, the title compound, m.p. 285°–287° C., is obtained in 60% yield.

EXAMPLE 25

2-Methylsulfonyl-3-(6'-methylergoline-8'β)-propionamide (I: $R_1=NH_2$, $R_3=CH_3SO_2$, $R_4=CH_3$, $R_2=R_5=R_6=R_7=H$)

Operating as in Example 2, but employing sodium methylsulfonylacetamide, the title compound, m.p. 242°–244° C., is obtained in 65% yield.

EXAMPLE 26

2-Methylsulfonyl-3-(6'-methylergoline-8'β)-N-propionyl-pyrrolidine (I: $R_1=$1-pyrrolidinyl, $R_3=CH_3SO_2$, $R_4=CH_3$, $R_2=R_5=R_6=R_7=H$)

Operating as in Example 2, but employing sodium methylsulfonylacetylpyrrolidine, the title compound, m.p. 235°–237° C., is obtained in 69% yield.

EXAMPLE 27

2-Methylsulfonyl-3-(6'methylergoline-8'β)-N-ethyl-propionamide (I: $R_1=CH_3CH_2NH$, $R_3=CH_3SO_2$, $R_4=CH_3$, $R_2=R_5=R_6=R_7=H$)

Operating as in Example 2, but employing sodium N-ethyl-methylsulphonylacetamide, the title compound, m.p. 227°–229° C., is obtained in 60% yield.

EXAMPLE 28

2-Acetyl-3(6'-methylergoline-8'β)-propionamide (I: $R_1=NH_2$, $R_3=CN$, $R_4=CH_3$, $R_2=R_5=R_6=R_7=H$)

Operating as in Example 2, but employing sodium acetylacetamide, the title compound, m.p. 225°–227° C., is obtained in 40% yield.

EXAMPLE 29

2-Cyano-3-(2'chloro-6'-methylergoline-8'β)-propionamide (I: $R_1=NH_2$, $R_3=CN$, $R_4=CH_3$, $R_6=Cl$, $R_2=R_5=R_7=H$)

Operating as in Example 8, but employing 2-chloro-6-methyl-8β-tosyloxymethylergoline, the title compound, m.p. 245°–246° C., is obtained in 45% yield.

EXAMPLE 30

2-Cyano-3-(6'-allylergoline-8'β)-N-ethylpropionamide (I: $R_1=CH_3CH_2NH$, $R_3=CN$, $R_4=CH_2=CHCH_2$, $R_2=R_5=R_6=R_7=H$)

Operating as in Example 5, but employing 6-allyl-β-toxyloxymethylergoline, the title compound, m.p. 130°–133° C., was obtained in 50% yield.

EXAMPLE 31

2-Acetyl-3-(6'-allylergoline-8'β)-propionic acid ethyl ester (I: $R_1=OCH_2CH_3$, $R_3=CH_3CO$, $R_4=CH_2=CHCH_2$, $R_2=R_5=R_6=R_7=H$)

Operating as in Example 16, but employing 6-allyl-8β-toxyloxymethylergoline, the title compound, m.p. 125°–128° C., was obtained in 60% yield.

EXAMPLE 32

2-Cyano-3-(6'allylergoline-8'β)-propionic acid ethyl ester (I: $R_1=OCH_2CH_3$, $R_3=CN$, $R_4=CH_2=CHCH_2$, $R_2=R_5=R_6=R_7=H$)

Operating as in Example 1, but employing 6-allyl-8β-toxyloxymethylergoline, the title compound, m.p. 186°–188° C., was obtained in 65% yield.

EXAMPLE 33

2-Cyano-3-(6'-ethylergoline-8'β)-N-ethylpropionamide (I: $R_1=CH_3CH_2NH$, $R_3=CN$, $R_4=CH_3CH_2$, $R_2=R_5=R_6=R_7=H$)

Operating as in Example 5, but employing 6-ethyl-8β-toxyloxymethylergoline, the title compound, m.p. 178°–180° C., was obtained in 55% yield.

EXAMPLE 34

2-Cyano-3-(6'n-propylergoline-8'β)-propionamide (I: $R_1=NH_2$, $R_3=CN$, $R_4=CH_3CH_2CH_2$, $R_2=R_5=R_6=R_7=H$)

There were added 9 ml of n-propyl iodide to a mixture of 10 g of 8β-methoxy-carbonylergoline and 8.2 g of potassium carbonate in 500 ml of DMF. After 20 hours under stirring at room temperature, the reaction mixture was poured into water and the precipitate was filtered and crystallized from methanol to give 10 g of 6-n-propyl-8β-methoxycarbonylergoline melting at 202°–204° C.

10 grams of 6-n-propyl-8β-methoxycarbonylergoline were added to a mixture of 10 g of sodium borohydride in 125 ml of methanol. The reaction mixture was refluxed for about 2 hrs; then a second 5 g batch of sodium borohydride was added. The reaction mixture was cooled after 5 hrs, diluted with water, and the precipitate was filtered to give 7.5 g of 6-n-propyl-8β-hydroxymethylergoline melting at about 166°–168° C. A solution of 15 g of 4-toluenesulfonyl chloride in 100 ml of pyridine was added slowly to a cooled solution of 7.5 g of 6-n-propyl-8β-hydroxymethylergoline in 300 ml of pyridine. The mixture was stirred for 7 hrs whereafter it was poured over iced water and the precipitate was filtered to give 9 g of 6-n-propyl-8β-toxyloxymethylergoline melting at 147°–150° C.

9 grams of 6-n-propyl-8β-toxyloxymethylergoline were treated with 2.4 g of sodium cyanoacetamide, as described in Example 8 and the title compound, m.p. 210°–212° C., was obtained in 48% yield.

EXAMPLE 35

2-Cyano-3-(6'-n-propylergoline-8'β)-N-ethyl-propionamide (I: $R_1=CH_3CH_2NH$, $R_3=CN$, $R_4=CH_3CH_2CH_2$, $R_2=R_5=R_6=R_7=H$)

Operating as in Example 5, but employing 6-n-propyl-8β-toxyloxymethylergoline, prepared as described in Example 34, the title compound, m.p. 173°–175° C., was obtained in 70% yield.

EXAMPLE 36

2-Acetyl-3-(6'-n-propylergoline-8'β)-propionic acid ethyl ester (I: $R_1=OCH_2CH_3$, $R_3=CH_3CO$, $R_4=CH_3CH_2CH_2$, $R_2=R_5=R_6=R_7=H$)

Operating as in Example 16, but employing 6-n-propyl-8β-toxyloxymethylergoline prepared as described in Example 34, the title compound, m.p. 159°–162° C., was obtained in 60% yield.

EXAMPLE 37

2-Cyano-3-(6'-isopropylergoline-8'β)-propionamide (I: $R_1=NH_2$, $R_3=CN$, $R_4=(CH_3)_2CH$, $R_2=R_5=R_6=R_7=H$)

Isopropyl iodide (71.8 ml) was added to a mixture of 7.7 g of 8β-methoxycarbonylergoline and 25 g of potassium carbonate in 357 ml of DMF. After 20 hrs under stirring at 90° C., the solution was evaporated under vacuo and poured into iced water; the pH of the mixture was adjusted with ammonia to 7 to 7.5 and the precipitate compound was filtered.

The crude product was purified by column chromatography on silica gel, using chloroform as eluent, to give 8 g of 6-isopropyl-8β-methoxycarbonylergoline, m.p. 193°–195° C., after crystallization from ether.

8 grams of 6-isopropyl-8β-methoxycarbonylergoline was added to a mixture of 8 g of sodium borohydride in 200 ml of methanol. The reaction mixture was heated under reflux for 2 hrs; then a second 2 g batch of sodium borohydride was added. The mixture was cooled after 3 hrs, diluted with water, and the precipitate was filtered to give 6.5 g of 6-isopropyl-8β-hydroxymethylergoline, m.p. 192°–194° C., after crystallization from methanol. A solution of 13 g of 4-toluenesulfonyl chloride in 87 ml of pyridine was added slowly to a cooled solution of 6.5 g of 6-isopropyl-8β-hydroxymethylergoline in 250 ml of pyridine. After 15 hrs the mixture was poured over iced water and the precipitate was filtered to give 7.4 g of 6-isopropyl-8β-toxyloxymethylergoline melting at 180°–184° C. after crystallization from acetone.

7.4 grams of 6-isopropyl-8β-toxyloxymethylergoline were treated with 1.9 g of sodium cyanoacetamide, as described in Example 8, and the title compound m.p. 248°–250° C., was obtained in 50% yield.

EXAMPLE 38

2-Cyano-3-(6'-isopropylergoline-8'β)-N-ethyl propionamide (I: $R_1=CH_3CH_2NH$, $R_3=CN$, $R_4=(CH_3)_2CH$, $R_2=R_5=R_6=R_7=H$)

Operating as in Example 5, but employing 6-isopropyl-8β-toxyloxymethylergoline, prepared as described in Example 37, the title compound, m.p. 115°–118° C., was obtained in 65% yield.

EXAMPLE 39

2-Acetyl-3-(6'-isopropylergoline-8'β)-propionic acid ethyl ester (I: $R_1=OCH_2CH_3$, $R_3=CH_3CO$, $R_4=(CH_3)_2CH$, $R_2=R_5=R_6=R_7=H$)

Operating as in Example 16, but employing 6-isopropyl-8β-toxyloxymethylergoline, prepared as described in Example 37, the title compound, m.p. 145°–147° C., was obtained in 55% yield.

EXAMPLE 40

2-Cyano-3-(2'-chloro-6'-methylergoline-8'β)-propionic acid ethyl ester (I: $R_1=OCH_2CH_3$, $R_3=CN$, $R_4=CH_3$, $R_6=Cl$, $R_2=R_5=R_7=H$)

Operating as in Example 1, but employing 2-chloro-6-methyl-8β-toxyloxymethlergoline, m.p. 159°–161° C., the title compound, m.p. 200°–202° C., was obtained in 45% yield.

EXAMPLE 41

2-Acetyl-3-(2'-bromo-6'-methylergoline-8'β)-propionic acid ethyl ester (I: $R_1=OCH_2CH_3$, $R_3=CH_3CO$, $R_4=CH_3$, $R_6=Br$, $R_2=R_5=R_7=H$)

Operating as in Example 16, but employing 2-bromo-6-methyl-8β-toxyloxymethylergoline, m.p. 148°–150° C., the title compound, m.p. 150°–152° C., was obtained in 45% yield.

EXAMPLE 42

2-Acetyl-3-(2',6'-dimethylergoline-8'β)-propionic acid ethyl ester (I: $R_1=OCH_2CH_3$, $R_3=CH_3CO$, $R_4=R_6=CH_3$, $R_2=R_5=R_7=H$)

Operating as in Example 16, but employing 2,6-dimethyl-8β-toxyloxymethylergoline, m.p. 130°–133° C., the title compound, m.p. 168°–170° C., was obtained in 60% yield.

EXAMPLE 43

2-Cyano-3-(2',6'-dimethylergoline-8'β)-propionamide (I: $R_1=NH_2$, $R_3=CN$, $R_4=R_6=CH_3$, $R_2=R_5=R_7=H$)

Operating as in Example 8, but employing 2,6-dimethyl-8β-toxyloxymethylergoline, the title compound, m.p. 270°–272° C., was obtained in 40% yield.

EXAMPLE 44

2-Cyano-3-(2',6'-dimethylergoline-8'β)-N-ethyl propionamide (I: $R_1=CH_3CH_2NH$, $R_3=CN$, $R_4=R_6=CH_3$, $R_2=R_5=R_7=H$)

Operating as in Example 5, but employing 2,6-dimethyl-8β-toxyloxymethylergoline, the title compound, m.p. 233°–235° C., was obtained in 54% yield.

EXAMPLE 45

2-Cyano-3-(6'-methylcyclopropylergoline-8'β)-propionamide (I: $R_1=NH_2$, $R_3=CN$, $R_4=CH_2-CH\underset{CH_2}{\overset{\diagdown\;\;\diagup}{\rule{0pt}{0pt}}}CH_2$, $R_2=R_5=R_6=R_7=H$)

There were slowly added 6 ml of cyclopropanecarboxylic acid chloride to an iced solution of 15 g of 8β-methoxycarbonylergoline in 170 ml of pyridine. The reaction mixture was left at room temperature for 1 hr, then poured into cooled acid water. The precipitate was filtered and crystallized from methanol to give 16 g of 6-cyclopropanoyl-8β-methoxycarbonylergoline melting at 276°–278° C.

A suspension of 16 of 6-cyclopropanoyl-8β-methoxycarbonylergoline was prepared in 2,000 ml of THF and 7.5 g of lithium aluminum hydride were added in portions at room temperature. The reaction mixture was refluxed for about 20 hrs and then cooled at 0° C.; the excess of lithium aluminum hydride decomposed by addition of THF and water. After filtration of the precipitate the solution was evaporated and the residue diluted with water and extracted with chloroform. The organic layer was removed under vacuo and the residue was crystallized from acetone to give 10 g of 6-methyl-cyclopropyl-8β-hydroxymethylergoline melting at 215°–217° C. A solution of 19 g of 4-toluenesulfonyl chloride in 100 ml of pyridine was added slowly to a cooled solution of 10 g of 6-methylcyclopropyl-8β-hydroxymethylergoline in 350 ml of pyridine. After 5 hrs the mixture was poured into water and the precipitate filtered to give 9.5 g of 6-methylcyclopropyl-8β-toxyloxymethylergoline melting at 168°–170° C. after crystallization from acetone.

9.5 Grams of 6-methylcyclopropyl-8β-toxyloxymethylergoline were treated with 2.5 g of sodium cyanoacetamide, as described in Example 8, and the title compound, m.p. 290°–292° C., was obtained in 60% yield.

EXAMPLE 46

2-Cyano-3-(6'-methylcyclopropylergoline-8β)-N-ethyl-propionamide)

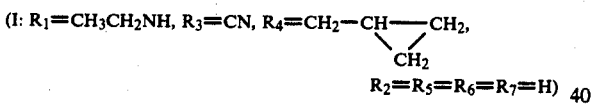

(I: $R_1=CH_3CH_2NH$, $R_3=CN$, $R_4=CH_2-CH-CH_2$, $CH_2$ $R_2=R_5=R_6=R_7=H$)

Operating as in Example 5, but employing 6-methyl-cyclopropyl-8β-toxyloxymethylergoline, prepared as described in Example 45, the title compound, m.p. 112°–115° C., was obtained in 60% yield.

EXAMPLE 47

3-Acetyl-4-(6'-n-propylergoline-8'β)-butanone (I: $R_1=CH_3$, $R_3=CH_3CO$, $R_4=CH_3CH_2CH_2$, $R_2=R_5=R_6=R_7=H$)

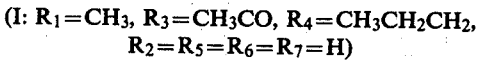

Operating as in Example 17, but employing 6-n-propyl-8β-toxyloxymethylergoline, prepared as described in Example 34, the title compound, m.p. 195°–197° C., was obtained in 70% yield.

EXAMPLE 48

3-Acetyl-4(6'-isopropylergoline-8'β)-butanone (I: $R_1=CH_3$, $R_3=CH_3CO$, $R_4=(CH_3)_2CH$, $R_2=R_5=R_6=R_7=H$)

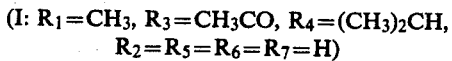

Operating as in Example 17, but employing 6-isopropyl-8β-toxyloxymethylergoline, prepared as described in Example 37, the title compound, m.p. 154°–156° C., was obtained in 60% yield.

What is claimed is:

1. A compound of formula (I):

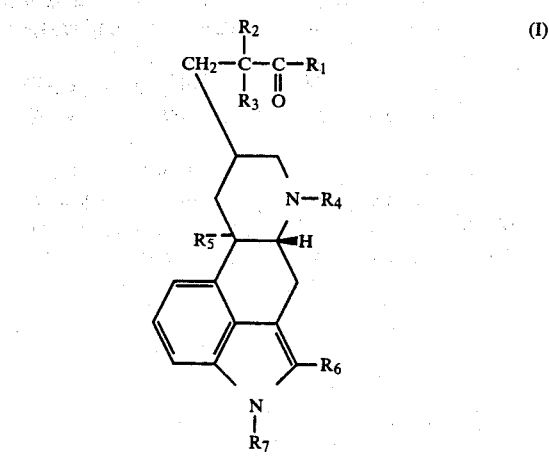

wherein
$R_1$ represents phenyl, piperidino, 1-pyrrolidinyl, morpholino or 4-methyl-1-piperazinyl, alkyl or alkoxy having from 1 to 4 carbon atoms, amino, substituted amino group of the formula NHR' (wherein R' represents an alkyl having from 1 to 4 carbon atoms, a cycloalkyl, benzyl, or phenyl) or amino of the formula NR" R'" (wherein R" and R'" both represent alkyl having from 1 to 4 carbon atoms);
$R_2$ represents a hydrogen atom, alkyl from 1 to 4 carbon atoms, or phenyl;
$R_3$ represents a fluorine atom, cyano, difluoromethyl, difluorobromomethyl, trifluoromethyl, methylthio, methylsulphonyl, sulphonamido, alkoxy having from 1 to 4 carbon atoms, alkanoyl having 2 to 5 carbon atoms, or benzoyl;
$R_4$ represents a hydrocarbon group having from 1 to 4 carbon atoms;
$R_5$ represents a hydrogen atom or methoxy;
$R_6$ represents a hydrogen or halogen atom or methyl; and
$R_7$ represents a hydrogen atom or methyl.

2. The compound of claim 1 wherein $R_4$ is selected from the group consisting of propyl, isopropyl, n-butyl, isobutyl, t.butyl, cyclopropyl, methylcyclopropyl, vinyl, and propargyl.

3. The compound of claim 1, which is 2-cyano-3-(6'-allylergoline-8'β)-N-ethylpropionamide.

4. The compound of claim 1, which is 2-acetyl-3-(6'-allylergoline-8'β)-propionic acid ethyl ester.

5. The compound of claim 1, which is 2-cyano-3-(6'-allylergoline-8'β)-propionic acid ethyl ester.

6. The compound of claim 1, which is 2-cyano-3-(6'-ethylergoline-8'β)-N-ethylpropionamide.

7. The compound of claim 1, which is 2-cyano-3-(6'-n-propylergoline-8'β)-propionamide.

8. The compound of claim 1, which is 2-cyano-3-(6'-n-propylergoline-8'β)-N-ethyl-propionamide.

9. The compound of claim 1, which is 2-acetyl-3-(6'-n-propylergoline-8'β)-propionic acid ethyl ester.

10. The compound of claim 1, which is 2-cyano-3-(6'-isopropylergoline-8'β)-propionamide.

11. The compound of claim 1, which is 2-cyano-3-(6'-isopropylergoline-8'β)-N-ethyl-propionamide.

12. The compound of claim 1, which is 2-acetyl-3-(6'-isopropylergoline-8'β)-propionic acid ethyl ester.

13. The compound of claim 1, which is 2-cyano-3-(2'-chloro-6'-methylergoline-8'β)-propionic acid ethyl ester.

14. The compound of claim 1, which is 2-acetyl-3-(2'-bromo-6'-methylergoline-8'β)-propionic acid ethyl ester.

15. The compound of claim 1, which is 2-acetyl-3-(2',6'-dimethylergoline-8'β)-propionic acid ethyl ester.

16. The compound of claim 1, which is 2-cyano-3-(2',6'-dimethylergoline-8'β)-propionamide.

17. The compound of claim 1, which is 2-cyano-3-(2',6'-dimethylergoline-8'β)-N-ethyl-propionamide.

18. The compound of claim 1, which is 2-cyano-3-(6-cyclopropylmethylergoline-8'β)-propionamide.

19. The compound of claim 1, which is 2-cyano-3-(6'-cyclopropylmethylergoline-8'β)-N-ethylpropionamide.

20. The compound of claim 1, which is 3-acetyl-4-(6'-n-propylergoline-8'β)-butanone.

21. The compound of claim 1, which is 3-acetyl-4-(6'-isopropylergoline-8'β)-butanone.

* * * * *